US006258384B1

(12) United States Patent
Stanley et al.

(10) Patent No.: US 6,258,384 B1
(45) Date of Patent: Jul. 10, 2001

(54) FROZEN PRODUCT AND METHOD OF ORAL DELIVERY OF ACTIVE INGREDIENTS

(75) Inventors: Steven A. Stanley; John A. Pachivas; John R. Annis, all of Hollywood, FL (US)

(73) Assignee: Med Tech Industries, Inc., Hollywood, FL (US)

( * ) Notice: Subject to any disclaimer, the term of this patent is extended or adjusted under 35 U.S.C. 154(b) by 0 days.

(21) Appl. No.: 09/618,617

(22) Filed: Jul. 18, 2000

Related U.S. Application Data

(63) Continuation-in-part of application No. 09/369,123, filed on Aug. 5, 1999, now Pat. No. 6,162,468.

(51) Int. Cl.$^7$ .......................... A61K 33/00; A61K 33/32; A61K 33/26; A61K 33/36; A61K 31/70; A61K 31/595; A61K 31/44; A61K 31/355; A61K 31/34; A61K 31/07

(52) U.S. Cl. .......................... 424/600; 424/643; 424/646; 424/667; 514/52; 514/168; 514/351; 514/356; 514/458; 514/474; 514/725

(58) Field of Search ..................................... 424/600, 643, 424/646, 667; 514/52, 168, 351, 356, 458, 474, 725

(56) References Cited

U.S. PATENT DOCUMENTS

| | | | |
|---|---|---|---|
| 4,021,583 | * | 5/1977 | Arden .................................. 426/134 |
| 4,218,482 | * | 8/1980 | Cook et al. ............................. 426/72 |
| 4,293,578 | * | 10/1981 | Stone ..................................... 426/66 |
| 4,537,194 | * | 8/1985 | Hanson et al. ....................... 128/399 |
| 4,992,282 | * | 2/1991 | Mehansho et al. ................... 426/72 |
| 5,431,915 | * | 7/1995 | Harvey et al. ........................ 424/439 |
| 5,698,247 | * | 12/1997 | Hall ........................................ 426/66 |
| 5,780,451 | * | 7/1998 | DeMichele et al. .................... 514/54 |
| 5,840,057 | * | 11/1998 | Aloisi ..................................... 614/20 |

OTHER PUBLICATIONS

Handbook of Nonprescrptin Drugs, 8th edition, pp. 338–339, 1986.*
Ross Products Division, Abbott Laboratories, Inc. "Diarrhea can be Dangerous", 1998, middle panel "Freezer Pops".*

* cited by examiner

*Primary Examiner*—Raymond Henley, III
(74) *Attorney, Agent, or Firm*—Robert M. Downey, PA

(57) ABSTRACT

A frozen nutritional food product and method for oral delivery of nutrients, medicinal substances and other active ingredients via absorption through the oral mucosa for systemic effect. The frozen product includes at least one active ingredient, at least one flavoring agent, preservatives, food coloring, and a balance of water as a delivery liquid. The water is subjected to a magnetic treatment process and an ozonation process to enhance delivery of the active ingredients. More particularly, a first portion of the water is magnetized to neutralize the pH, increase oxygenation, and to improve the solubility of the ingredients mixed with the water. The remaining portion of the water is sterilized by ozonation, causing oxidation of undesirable metallic ions, odor and taste producing agents, and a wide variety of organics. Ozonation further increases the dissolved oxygen content of the water. The ingredients of the composition are thoroughly mixed and dissolved in the treated water to provide a solution which is frozen in the form of a Popsicle contained on a stick or within a plastic bag. When the frozen Popsicle comes into contact with the tissue of the oral cavity, the active ingredient(s) is absorbed through the mucosal and sub-lingual membranes and into the bloodstream.

17 Claims, 1 Drawing Sheet

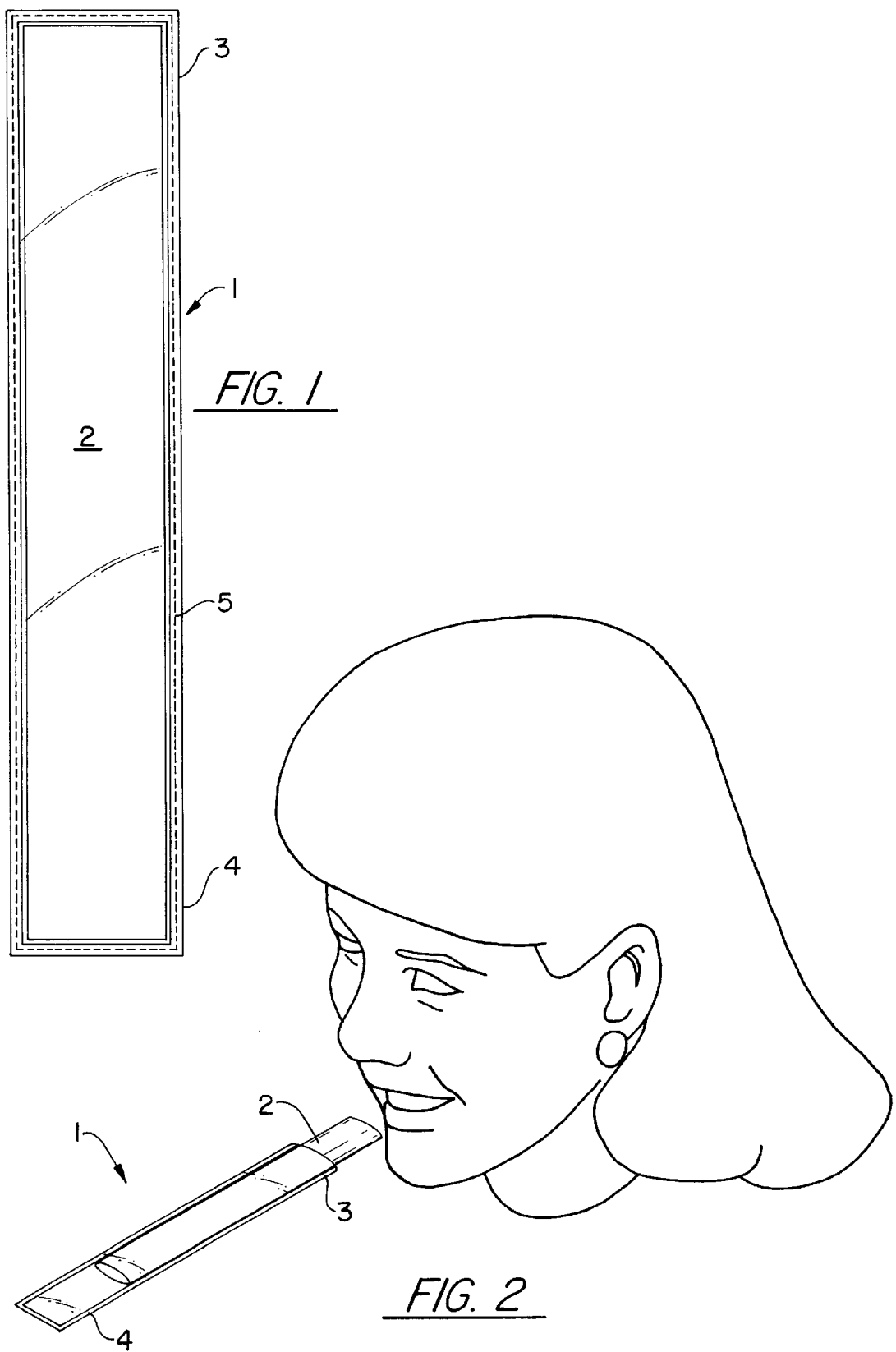

FROZEN PRODUCT AND METHOD OF ORAL DELIVERY OF ACTIVE INGREDIENTS

This application is a continuation-in-part patent application of U.S. patent application Ser. No. 09/369,123 filed on Aug. 5, 1999, now U.S. Pat. No. 6,162,468.

BACKGROUND OF THE INVENTION

1. Field of the Invention

The present invention relates generally to a nutritional dietary supplement delivery system and, more specifically, to a frozen product and a method for the oral delivery of nutrients and/or other active ingredients into the bloodstream of mammals for systemic effect.

2. Discussion of the Related Art

The traditional program for obtaining necessary vitamins, minerals and other nutrients is to attempt to eat a balanced diet and then to make up for the inevitable nutritional deficiencies by taking nutritional supplements and vitamin pills. However, for children, pill taking is difficult and sometimes impossible. Thus, instead of pills, liquid nutritional supplement solutions have been developed, particularly for use by children. Unfortunately, children resist taking liquid supplements due to the unappealing taste of such products. In addition, even if the liquid supplement is provided with flavoring to improve taste, many children still resist taking the liquid substance due to stubbornness.

The problem associated with taking pills is further exasperated when it is necessary to administer a medicine. In some cases, liquid formulations, such as syrups, are available. However, these syrups usually taste unpleasant and are often rejected by both children and adults.

Elderly patients, or those who have been weakened by a debilitating disease, radiation therapy, chemotherapy, or another medical condition or treatment may require the administration of oral medication. In such instances, it is often not possible for the patient to swallow pills. Further, syrups and other liquid products can be irritating to the mouth and difficult to swallow, particularly if the patient is suffering from painful lesions in the oral mucosa, such as those associated with candidiasis, also known as thrush.

For athletes, nutritional supplements are typically packaged as sports drinks. Sports drinks help to replace fluids and electrolytes by containing water and nutrients. However, even when refrigerated, sports drinks do not cool the person as quickly and effectively as a frozen product. In the case of a drink containing ice, the liquid is cooled to just above the freezing point, but the liquid being consumed does not undergo a phase change inside the drinker's body. A phase change of solid to liquid (i.e., ice to water) absorbs significantly more heat than the heat transfer from the simple warming of a liquid. Moreover, the electrolytes or active ingredients are not absorbed into the bloodstream until the liquid settles in the person's stomach. This method of delivery is less effective and not as rapid as delivery through the oral mucosa.

In the past, others have proposed various approaches to the administration of all medication as well as other active ingredients by oral administration. For example, frozen electrolyte compositions are available under the trade name PEDIALYTE®, a registered trademark of Ross Products Division, Abbott Laboratories, Inc., Columbus, Ohio. These freeze pops contain a solution with electrolytes. The composition is designed to prevent dehydration particularly in infants. The PEDIALYTE® composition does not include other active ingredients such as nutrients, including carbohydrates, vitamins, minerals and medicine. Further, the delivery and absorption of the active ingredients is not enhanced by magnetic treatment and/or ozonation of the delivery fluid, as in the present invention.

U.S. Pat. No. 5,431,915 to Harvey, et al. discloses a frozen oral medication delivery system and method for oral administration of pharmaceutically active agents. The medication is mixed and frozen in a storage container until hard, at which time it can be administered to the patient in the form of a frozen Popsicle. In particular, the oral medication delivery system in Harvey, et al. is particularly well suited for delivering Nystatin to oral candidiasis lesions, especially in very young as well as elderly patients who are unable to take medications by traditional administration methods.

U.S. Pat. No. 5,132,114 to Stanley, et al. discloses a method for the transmucosal delivery of medication which can have local and/or systemic effect. The therapeutic agent is incorporated into a candy matrix in powder form and is compressed to form a lollipop which includes a suitable holder.

U.S. Pat. No. 4,238,475 to Witzel, et al. discloses a chewing gum formulation that releases a small continuous dose of a medication, such as Nystatin, or an orally beneficial material into the mouth. This means of delivering medication to the mouth and oral mucosa can be very effective. However, persons with dentures or bridgework, persons with orthodontic appliances, and very young children are unable to chew gum, which limits the use of this medication delivery system to that segment of the population capable of chewing gum comfortably. Moreover, Witzel, et al. fail to provide means for enhancing the delivery and absorption of the active ingredients through the oral mucosa. Specifically, there is no teaching or suggestion in the patent to Witzel, et al. of magnetic treatment and/or ozonation of the delivery vehicle to enhance delivery and absorption of the active ingredients.

U.S. Pat. No. 4,478,822 to Haslam, et al. discloses a drug delivery system which can be used to deliver drugs to, inter alia, the oral cavity. This drug delivery system uses an aqueous vehicle that includes a polymer which causes the aqueous system to deliver a gel at temperatures encountered in body cavities. While this drug delivery system may be somewhat effective for its intended use, it is not likely to be the most effective method of delivery and absorption of active ingredients through the oral mucosa.

SUMMARY OF THE INVENTION

The present invention is directed to a frozen comestible composition containing at least one active ingredient. For purposes of this invention, an active ingredient is a substance that has a local or systemic effect once administered to the patient or user.

The active ingredient can include a nutrient mixture consisting of essential vitamins and minerals. The mixture may further be provided with flavor agents or other pleasant tasting ingredients. To add to the aesthetic attractiveness, as well as to help the consumer identify the flavor, food coloring can be added to the composition. Preferably, the composition is administered in the form of a frozen Popsicle or squeeze pop. The composition can be varied for different applications such as children, athletes, geriatric users, invalids, or infirm individuals.

The vitamins and minerals contained in the nutrient mixture may include vitamin A, vitamin C, vitamin D, vitamin E, vitamin B1, vitamin B2, vitamin B6, vitamin B12, Niacinamide, pantothenic acid, paba, choline, inositol, folic acid, d-Biotin, calcium, magnesium, iron, manganese, zinc, potassium, selenium, and iodine. The nutrients can also include nutritional energy sources such as carbohydrates, protein, and electrolytes.

Children prefer the frozen composition over other means of obtaining vitamins and nutrients because the composition contains flavors and sweeteners and is provided in the form of a frozen product which resembles a favorite refreshing dessert, namely an ice pop or Popsicle.

For athletes, the frozen composition provides a means to quickly absorb nutrients, replace fluids, and to rapidly cool the athlete.

Infirm patients who have upset stomachs or lack of appetite may find the frozen composition to be a more convenient and soothing way to obtain nutrients.

The composition can include an active ingredient that is a medicinal substance. Examples of medicines which may be included as active ingredients in the composition include, but are not limited to, over-the-counter medications as well as those sold by prescription. By delivering medicine in the form of a frozen pop, patients who are unable to swallow pills are provided with an alternative means for administration of required medicines. Further, because the composition is provided with flavors and sweeteners, the frozen product provides a tasty, enjoyable means for taking medicine. In addition, a specific dosage of medicine can be provided in each frozen Popsicle and this dosage can be varied depending on the patient and situation. For example, a smaller dosage may be provided for children, while a larger dosage would be available for adults. Absorption of the medication is enhanced by delivery through the oral mucosa, particularly when the delivery fluid is subjected to magnetic treatment and ozonation.

For purposes of the invention, electrolytes may be considered as an active ingredient when provided alone or in combination with other active ingredients. Diarrhea and perspiring are two common causes for dehydration and loss of electrolytes. By consuming the frozen product of the present invention, containing additional electrolytes, fluid and electrolytes can be quickly replaced in the body. In addition, by allowing the frozen product of the present invention to melt in the consumer's mouth, the electrolytes can be absorbed quickly through the person's oral mucosal glands. Oral absorption is especially significant in persons who have diarrhea or other digestive disorders that prevent absorption and the stomach.

In accordance with a preferred embodiment of the present invention, the frozen product includes at least one active ingredient, at least one flavoring agent, preservatives, food coloring, and a balance of water. The water is subjected to a magnetic treatment process and an ozonation process to enhance delivery of the active ingredients. More particularly, a first portion of the water is magnetized to neutralize the pH, increase oxygenation, and to improve the solubility of the ingredients mixed with the water. The remaining portion of the water is sterilized by ozonation, causing oxidation of undesirable metallic ions, odor and taste producing agents, and a wide variety of organics. Ozonation further increases the dissolved oxygen content of the water. The ingredients of the composition are thoroughly mixed and dissolved in the treated water to provide a delivery fluid which is frozen in the form of a Popsicle contained on a stick or on a plastic squeeze bag. When the frozen product comes into contact with the tissue of the oral cavity, the active ingredients are absorbed through the mucosal and sub-lingual membranes and into the bloodstream.

With the foregoing in mind, it is a primary object of the present invention to provide a frozen product and method of oral delivery of active ingredients by absorption through the mucosal glands and sub-lingual membranes of the mouth.

It is a further object of the present invention to provide a frozen product for oral delivery of active ingredients, wherein the frozen product is provided with an appealing taste and color.

It is still a further object of the present invention to provide a frozen product for the oral delivery of active ingredients including nutrients, such as vitamins and minerals.

It is still a further object of the present invention to provide a means for delivery of nutrients, medication, and other active ingredients to young children and elderly people who are unable to swallow pills, syrups, or other products.

It is still a further object of the present invention to provide a means for athletes to recover water and active ingredients, including but not limited to, nutrients such as carbohydrates, minerals, medicine, electrolytes, proteins, sugars, and the like.

It is still a further object of the present invention to provide a means for rapidly cooling athletes while delivering water for quick rehydration as well as active ingredients.

It is yet a further object of the present invention to provide a frozen product in the form of an ice pop which has an appealing taste and which is also nutritious.

It is still a further object of the present invention to provide a means for delivering a nutrient composition through the mucosal and sub-lingual membranes of the mouth.

It is still a further object of the present invention to provide a pleasant, tasty means for orally administering a pre-measured dosage of a medicine.

In accordance with these and other object and advantages of the present invention, which will become more readily apparent hereinafter, the instant invention will now be described with particular reference to the accompanying drawings.

BRIEF DESCRIPTION OF THE DRAWINGS

FIG. 1 is a top plan view of the frozen product of the present invention, containing the composition held in a frozen form in a temporarily sealed squeeze bag; and FIG. 2 is a perspective view showing a person who is in the process of extruding the frozen composition from the squeeze bag of FIG. 1, after having unsealed one end of the bag to permit squeezing of the frozen composition outwardly from the open end, thereby enabling the frozen composition to be inserted into the mouth for direct contact with the tissue in the oral cavity.

DETAILED DESCRIPTION OF THE PREFERRED ENBODIMENTS

The present invention encompasses a composition provided in a frozen product for oral delivery of active ingredients in the composition, as well as a method of oral delivery of active ingredients via absorption through the oral mucosal glands and sub-lingual membranes of the mouth. In a preferred embodiment, the active ingredient(s) is carried in a nutrient mixture or in the form of a medicinal substance.

In one particular preferred embodiment, the composition contained in the frozen product of the present invention, includes the following ingredients: active ingredients, flavoring agents, preservatives, food coloring, and a balance of water. More specifically, in one preferred embodiment of the present invention, the active ingredient is in the form of a nutrient mixture containing vitamins and/or minerals. The following table includes examples of ingredients contained in the composition, including the amount (wherein iu=international unit, mcg=microgram, and mg=milligram) and percentage of recommended daily intake for children 2–3 years old taking a half dose, and people 4 years and older taking a full dose. In this particular example, a dose is 1–½ fluid ounces.

TABLE 1

| INGREDIENT | AMOUNT | % DAILY VALUE FOR CHILDREN 2–3 YEARS (½ DOSE) | % DAILY VALUE FOR 4 YEARS OLD AND OLDER (FULL DOSE) |
| --- | --- | --- | --- |
| Vitamin A | 5000 iu | 100 | 100 |
| Vitamin B | 150 mg | 120 | 100 |
| Vitamin D | 400 iu | 50 | 100 |
| Vitamin E | 30 iu | 150 | 100 |
| Vitamin B1 | 5 mg | 166 | 333 |
| Vitamin B2 | 5 mg | 147 | 294 |
| Vitamin B6 | 5 mg | 125 | 250 |
| Vitamin B12 | 10 mcg | 83 | 167 |
| Niacinamide | 15 mg | 37 | 75 |
| Pantothenic Acid | 15 mg | 75 | 150 |
| Paba | 5 mg | n/a | n/a |
| Choline | 10 mg | n/a | n/a |
| Inositol | 10 mg | n/a | n/a |
| Folic acid | 100 mcg | 12 | 25 |
| d-Biotin | 50 mcg | 8.35 | 16.7 |
| Calcium | 25 mg | 1.2 | 2.5 |
| Magnesium | 12 mg | 1.5 | 3 |
| Iron | 5 mg | 11.5 | 23 |
| Manganese | 1 mg | n/a | n/a |
| Zinc | 2 mg | 6 | 12 |
| Potassium | 2 mg | n/a | n/a |
| Selenium | 5 mcg | n/a | n/a |
| Iodine | 0.05 mg | 16.5 | 33 |

The ingredients set forth in Table 1 are examples of those which may be used in the nutrient mixture in accordance with various formulations thereof. A combination of some or all of these ingredients provide vitamins and minerals which are recommended on a daily basis. The relative amounts and types of nutrients can be interchanged and adjusted for specific individuals. Moreover, specific formulations can be made for consumers having different needs. For instance, children, geriatric users, athletes, men and women are examples of different types of individuals which require different formulations. It should be noted that it is preferable that each of the ingredients be water soluble so that they may be contained in a delivery liquid.

In an alternative embodiment, the active ingredient includes one or more medicines. The medicine can be of the type sold over the counter or of a prescribed type. The medicine can be organic or inorganic and the amount of medicine(s) in each freeze pop can be tailored to the proper dosage for the individual. For example, the composition contained in the frozen pop would have a lower dosage of a particular medicine for children as compared to the dosage required for adults.

The composition preferably contains at least one flavoring agents. These flavoring agents are flavors and sweeteners that include, but are not limited to, high fructose corn syrup, dextrose, sugar, fruit juice, pectin, citric acid, cellulose gum, natural flavors, artificial flavors, and sodium citrate. Flavoring agents are not required, but are included for several reasons. First, the composition, when frozen is to be held in the user's mouth and allowed to melt. By adding flavoring agents, the composition is more palatable, particularly for young children. Without flavoring agents, the user might be induced to swallow the composition in order to avoid an unpleasant taste or lack of taste, before the nutrients are able to be absorbed through the user's mucosal glands and sub-lingual membranes. The amounts of these ingredients can also be adjusted to enhance the texture and freezing qualities of the composition.

The composition may also contain preservatives. The preservatives contemplated for use in the present invention include, but are not limited to, sodium benzoate and potassium sorbate. Although not required, preservatives are included in the composition to extend the shelf life of the composition and to prevent spoilage.

The composition of the frozen product may further be provided with food colorings. These food colorings include, but are not limited to, USFDA certified food colors red No. 40, yellow No. 6, and blue No. 1. Although not required, food colorings are included to enhance the aesthetic appearance of the product, particularly when carried in a transparent package. Food coloring also helps the consumer associate the color with the flavor prior to purchase and consumption. For example, strawberry flavor can be dyed red and blueberry flavor would be dyed blue.

The balance of the composition is water treated by a magnetic process and an ozonation process to enhance delivery of the active ingredients. The water is used to dilute the other ingredients to their preferred concentrations providing a delivery fluid. By adding a substantial percentage of water, the freezing point of the composition can be adjusted to approximately the same as water (e.g., 32° Fahrenheit or 0° Celsius). This allows conventional freezing techniques to be used while also providing for a predictable melting temperature of the composition during consumption. It should be noted that the term "balance of the composition" is not to be read in a manner which limits the inclusion of other ingredients besides those specifically claimed.

In accordance with a preferred embodiment of the present invention, a first portion of the water is magnetized to neutralize the pH and to improve the solubility of the ingredients mixed with the water. To do this, water is directed through a conduit which is surrounded by a magnetizing device. The magnetizing device generates voltages and currents which result in an electrolysis reaction, producing nucleation centers. Pure water is a polar liquid (i.e., part of the water molecule has a positive electric charge and part of the water molecule has a negative electric charge). Thus, the water molecule being a small magnet (i.e., dipole) may have its magnetic field altered by causing the molecule to turn or rotate in one direction or the other, taking on a positive or negative higher potential, depending on whether the south (positive) or north (negative) outside magnetic field has been applied. It has been firmly established in the world scientific community that the positive, expanding field influence of the south pole, makes liquids more soluble (lowering surface tension), thereby increasing hydration, solubility and selective ionization. An example of a suitable magnetizing device for use in the manufacture of the product of the present invention is available under the trademark WHOLLY WATERS®. Information on this product and the benefits of magnetically treated water is available on the Internet at www.wholly-water.com, which is incorporated herein by reference.

The remaining portion of the water is sterilized by ozonation, causing oxidation of undesirable metallic ions, odor and taste producing agents, and a wide variety of organics. Treatment by ozonation further increases the dissolved oxygen content of the water. Information on various ozone treatment devices and the benefits of ozonation is available on the Internet at the following websites: www.aqua-floinc.com; www.biozone.com; and www.bluediamond.com, all of which are incorporated herein by reference.

Referring to FIG. 1, a preferred method for packaging the composition is shown. Specifically, a releasably, sealable, long, relatively slender plastic package is provided and is generally indicated as 1. According to this packaging method, the composition 2 is inserted into the bag 1 and the bag 1 is sealed around the perimeter 5. The composition 2 can be packaged as a liquid or a frozen solid. In either case, the manufacturer and/or consumer would place the bag 1 containing the liquid composition 2 into a freezer to subject the composition 2 to temperatures below 32° Fahrenheit. The composition 2 will eventually freeze within the package 1 and is kept in this frozen state until the time of consumption. Plastic transparent bags have the advantage of not bursting when water expands during freezing. Further, the transparent nature of the bag enables the consumer to identify the flavor by visibly exposing the color of the composition. To consume the frozen composition 2, the first end 3 of the bag 1 is opened (e.g., by tearing or cutting with a scissor or knife) and the frozen composition 2 is extended out from the open end 3 by pressing the opposite second end 4 so that the composition is forced longitudinally with a portion of the composition extending out from the open end 3.

When ingesting the frozen composition, the frozen composition is placed within the consumer's mouth and allowed to melt. Specifically, the exposed or extended portion of the frozen composition is inserted within the mouth and placed against the exposed tissues within the oral cavity, including the tongue and the inner cheek surfaces. After the composition has melted, the consumer can swallow the dissolved liquid portion. Consuming the composition in such a manner, the active ingredient is exposed to the tissue within the oral cavity for an extended period of time where it can be absorbed into the consumer's bloodstream through the oral mucosal membranes and sub-lingual membranes. The composition continues to be absorbed by the consumer's digestive system after swallowing.

For athletes, the frozen composition provides the additional benefit of cooling the athlete as the composition melts. The cooling can be combined with a composition containing enhanced amounts of electrolytes which are routinely lost during exercise when the athlete perspires.

For infirmed patients who have upset stomachs or lack of appetite, the frozen composition provides the patient with a means for absorbing nutrients which does not rely on the patient swallowing the composition.

While the instant invention has been shown and described in accordance with preferred and practical embodiments thereof, it is recognized that departures from the instant disclosure may be made and the scope of the invention is not to be limited except as set forth in the following claims as interpreted under the doctrine of equivalents.

What is claimed is:

1. A method for the oral delivery of one or more active ingredients into the bloodstream of a mammal, comprising the steps of:

providing a composition including the one or more active ingredients and a balance of water;

treating at least a portion of the water using a magnetic treatment device to produce magnetically treated water;

treating at least a remaining portion of the water using an ozonation device to produce ozonated water;

combining said magnetically treated water with said ozonated water;

mixing the remaining ingredients of the composition, including the one or more active ingredients, in the combined treated water to produce a solution;

freezing the solution to produce a solid form;

placing the frozen solid form, containing the composition, within the oral cavity of the mammal so that the frozen solid form is maintained against the tissue within the oral cavity; and allowing the frozen solid form to melt and causing the one or more active ingredients to be absorbed through the mucosal membranes and sub-lingual membranes of the mouth for entry into the bloodstream.

2. The method as recited in claim 1 wherein said step of providing a composition further includes the step of:

providing a nutrient mixture in the composition, defining the one or more active ingredients thereof, said nutrient mixture consisting of: vitamin A; vitamin C; vitamin D; vitamin E; vitamin B1; vitamin B6; vitamin B12; Niacinamide; Pantothenic acid, paba; choline; inositol; folic acid; d-Biotin; calcium; magnesium; iron; manganese; zinc; potassium; selenium; and iodine.

3. The method as recited in claim 1 wherein said step of providing a composition further includes the step of:

providing at least one flavoring agent.

4. The method as recited in claim 3 wherein said step of providing at least one flavoring agent further includes the step of:

providing said at least one flavoring agent, wherein said flavoring agent is chosen from the group consisting of high fructose corn syrup; dextrose; sugars; fruit juice; pectin; citric acid; cellulose gum; natural flavors; artificial flavors; and sodium citrate.

5. The method as recited in claim 1 wherein said step of providing a composition further includes the step of:

providing a preservative.

6. The method as recited in claim 5 wherein the step of providing said preservative further includes the step of:

providing said preservative chosen from the group consisting of sodium benzoate and potassium sorbate.

7. The method as recited in claim 1 wherein step of providing a composition further includes the step of:

providing a food coloring.

8. The method as recited in claim 7 wherein said step of providing a food coloring further comprises the step of:

providing said food coloring chosen from the group consisting of USFDA certified food colors, red No. 40, yellow No. 6, and blue No. 1.

9. A nutritional food product comprising:

at least one active ingredient;

at least one flavoring agent;

electrolytes; and a balance of water, including a portion of ozonated water and a portion of magnetically treated water.

10. The composition as recited in claim 9, wherein said at least one active ingredient is a nutrient mixture selected from the group consisting of:

Vitamin A;
Vitamin C;
Vitamin D;
Vitamin E;
Vitamin B1;
Vitamin B6;
Vitamin B12;
Niacinamide;
Pantothenic Acid;
Paba;
Choline;
Inositol;
Folic Acid;
d-Biotin;
Calcium;
Magnesium;
Iron;
Manganese;
Zinc;
Potassium;
Selenium;
Iodine.

11. The composition as recited in claim 9 further comprising at least one food coloring agent.

12. The composition as recited in claim 9 wherein said at least one flavoring agent is selected from the group consisting of:
High fructose corn syrup;
Dextrose;
Sugar;
Five percent fruit juice;
Pectin;
Citric Acid;
Cellulose gum;
Natural flavors;
Artificial flavors; and
Sodium citrate.

13. The composition as recited in claim 9 further comprising at least one preservative.

14. The composition as recited in claim 9 wherein said at least one active ingredient includes a medicine.

15. The composition as recited in claim 9 wherein said at least one active ingredient is organic.

16. The composition as recited in claim 9 wherein said at least one active ingredient is inorganic.

17. The composition as recited in claim 9 further comprising carbohydrates.

* * * * *